(12) United States Patent
Rice et al.

(10) Patent No.: US 10,292,737 B2
(45) Date of Patent: May 21, 2019

(54) SPINAL IMPLANT SYSTEM AND METHOD

(71) Applicant: Warsaw Orthopedic, Inc, Warsaw, IN (US)

(72) Inventors: Molly K. Rice, Memphis, TN (US); Dennis G. Crandall, Mesa, AZ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 59 days.

(21) Appl. No.: 15/616,397

(22) Filed: Jun. 7, 2017

(65) Prior Publication Data

US 2018/0353217 A1    Dec. 13, 2018

(51) Int. Cl.
*A61B 17/70* (2006.01)
*A61B 17/88* (2006.01)

(52) U.S. Cl.
CPC ...... *A61B 17/7053* (2013.01); *A61B 17/7035* (2013.01); *A61B 17/7041* (2013.01); *A61B 17/8869* (2013.01)

(58) Field of Classification Search
CPC ............ A61B 17/7034; A61B 17/7002; A61B 17/7035; A61B 17/7053; A61B 17/7086
USPC ......... 606/263, 267, 270, 277, 74, 103, 105, 606/86 A; 600/263, 267, 270, 277, 74, 600/103, 105, 86 A
See application file for complete search history.

(56) References Cited

U.S. PATENT DOCUMENTS

| | | | |
|---|---|---|---|
| 5,312,410 A * | 5/1994 | Miller | A61B 17/8861 606/103 |
| 5,782,831 A | 7/1998 | Sherman et al. | |
| 7,481,828 B2 | 1/2009 | Mazda et al. | |
| 8,870,881 B2 | 10/2014 | Rezach et al. | |
| 9,492,207 B2 * | 11/2016 | Baccelli | A61B 17/7053 |
| 2007/0233066 A1 | 10/2007 | Rezach | |
| 2009/0138048 A1 | 5/2009 | Baccelli et al. | |
| 2009/0326585 A1 | 12/2009 | Baccelli et al. | |
| 2010/0249845 A1 | 9/2010 | Meunier et al. | |
| 2011/0034956 A1 | 2/2011 | Mazda et al. | |
| 2011/0112581 A1 | 5/2011 | Clement | |
| 2011/0184469 A1 | 7/2011 | Ballard et al. | |
| 2011/0270314 A1 | 11/2011 | Mueller et al. | |
| 2013/0041410 A1 * | 2/2013 | Hestad | A61B 17/7032 606/263 |
| 2013/0072983 A1 | 3/2013 | Lindquisr et al. | |
| 2013/0261680 A1 * | 10/2013 | Baccelli | A61B 17/7053 606/86 A |
| 2013/0268005 A1 | 10/2013 | Rezach et al. | |
| 2014/0114356 A1 * | 4/2014 | Le Couedic | A61B 17/7053 606/263 |
| 2014/0148854 A1 | 5/2014 | Carlson et al. | |
| 2015/0164561 A1 | 6/2015 | Simpson et al. | |
| 2015/0282847 A1 | 10/2015 | Gordon et al. | |
| 2015/0289906 A1 | 10/2015 | Murray et al. | |

(Continued)

FOREIGN PATENT DOCUMENTS

WO    2013070628 A1    5/2013

*Primary Examiner* — Kevin T Truong
*Assistant Examiner* — David C Comstock

(57) ABSTRACT

A spinal implant comprises a fastener including a head and defining a longitudinal axis. A member is configured for disposal of the head and defines an inner groove configured for disposal of a band that is engageable with the head to connect the fastener and the member. The member is moveable relative to the longitudinal axis. The member defines a passageway configured for disposal of a tether. Systems, spinal constructs, surgical instruments and methods are disclosed.

20 Claims, 7 Drawing Sheets

(56) References Cited

U.S. PATENT DOCUMENTS

2016/0106478 A1 4/2016 Simpson et al.
2016/0310170 A1 10/2016 Carls
2017/0086889 A1* 3/2017 Padilla ............... A61B 17/7053
2018/0153591 A1* 6/2018 Schafer ............. A61B 17/8869

* cited by examiner

US 10,292,737 B2

SPINAL IMPLANT SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. Correction treatments used for positioning and alignment may employ implants, such as vertebral rods, bone screws and sublaminar wire for stabilization of a treated section of a spine. This disclosure describes an improvement over these prior technologies.

SUMMARY

In one embodiment, a spinal implant is provided. The spinal implant comprises a fastener including a head and defining a longitudinal axis. A member is configured for disposal of the head and defines an inner groove configured for disposal of a band that is engageable with the head to connect the fastener and the member. The member is moveable relative to the longitudinal axis. The member defines a passageway configured for disposal of a tether. In some embodiments, systems, spinal constructs, surgical instruments and methods are disclosed.

In one embodiment, a spinal implant system is provided. The spinal implant system comprises a connector defining a cavity and a bay. A tether is configured for disposal within the cavity. A spinal rod is configured for disposal within the bay. A fastener includes a head and defines a longitudinal axis. A member is configured for disposal of the head and defines an inner groove configured for disposal of a band that is engageable with the head to connect the fastener and the member. The member is moveable relative to the longitudinal axis. The member defines a passageway configured for disposal of the tether. In one embodiment, the spinal implant system includes a tensioner connected with the connector and including a ratchet engageable with the tether to adjust tension of the tether.

BRIEF DESCRIPTION OF THE DRAWINGS

The present disclosure will become more readily apparent from the specific description accompanied by the following drawings, in which.

DETAILED DESCRIPTION

Figure 1:
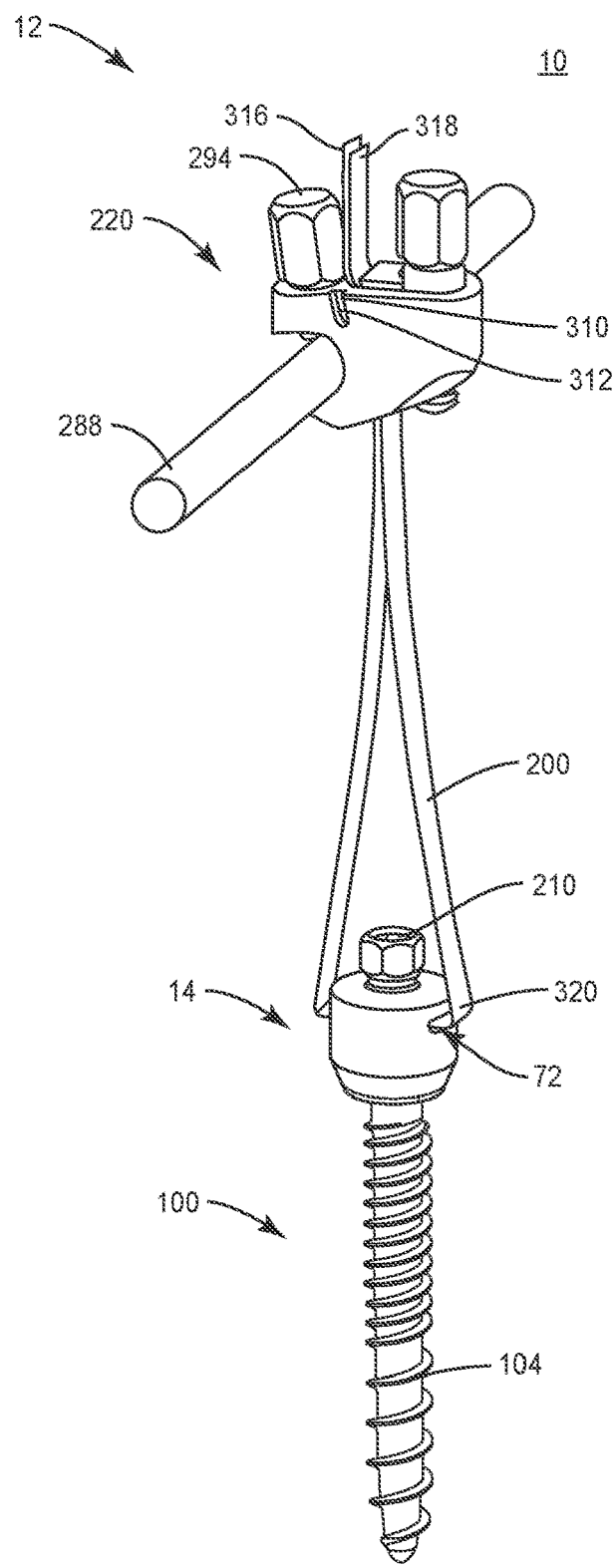
FIG. 1 is a perspective view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the present surgical system includes a spinal implant including a tether-based reduction screw. In some embodiments, the present surgical system is employed with deformity applications. In some embodiments, the present surgical system includes a tether-based reduction screw that enables an incomplete reduction of a vertebral body to a spinal rod. In some embodiments, the screw provides the ability to lock a dorsal height of a spinal construct at any point along a length of a tether.

In some embodiments, the present surgical system includes a spinal construct having a sublaminar tether connection to a spinal rod. In some embodiments, the present surgical system includes a spinal construct having a tether connection to a bone screw. In some embodiments, the spinal construct includes a set screw disposed at a bone screw head/shank interface to lock motion of a multi-axial screw head of the bone screw. In some embodiments, the set screw locks motion of a multi-axial screw head and fixates position of the tether relative to the bone screw.

In some embodiments, the present surgical system includes a spinal construct having a tether connection to a bone screw that employs a combination of high tension and locking at a rod/tether interface to lock motion of a multi-axial screw head and fixate position of the tether relative to the bone screw. In some embodiments, the present surgical system includes a spinal construct having a multi-axial head of a bone screw that employs tension on a tether to restrict motion of the multi-axial head and is not locked by a separate mechanism.

In some embodiments, the present surgical system includes a spinal construct that allows for a direct connection between a flexible tether and a pedicle screw. In some embodiments, the spinal construct allows a secondary, independent connection of the tether to a spinal rod. In some embodiments, the spinal construct links the spinal rod and the bone screw through a tether braid. In some embodiments, the present surgical system includes a tensioning mechanism that reduces a vertebral body to a spinal rod. In some embodiments, the tensioning mechanism provides the ability to discontinue reduction at any point along a length of a tether. In some embodiments, the spinal construct includes an interface that can be fixated at a selected dorsal height relative to a vertebral body. In some embodiments, this configuration avoids potential weakening of the bone-screw interface and screw pull out.

In some embodiments, the present surgical system includes a spinal construct that is employed with a method including the steps of connecting a spinal construct having a tether to a bone screw. In some embodiments, the method includes the step of connecting the tether to a spinal rod. In some embodiments, the distance, for example dorsal height, between the bone screw and the spinal rod is adjustable. In some embodiments, the distance, for example dorsal height, between the bone screw and the spinal rod is lockable at a selected location along a tether length. In some embodiments, the present surgical system includes a device for reduction of the spinal construct that is adjustable and allows for incomplete and/or partial reduction.

In some embodiments, the present surgical system includes a spinal construct that includes a set screw used at a screw head/shank interface to lock the multi-axial motion of the bone screw head. In some embodiments, the same set screw that is employed at the screw head/shank interface to fix the screw head relative to the shank can lock the tether in position with the bone screw. In some embodiments, tension applied to the tether as part of a reduction maneuver may obviate the need to lock the tether position at the bone screw interface. In some embodiments, the present surgical system includes a spinal construct that tensions a tether to lock multi-axial motion of a screw head.

In some embodiments, the present surgical system includes a spinal construct having a tether, a spinal rod and one or more bone fasteners, and a reduction mechanism. In some embodiments, the spinal rod can be reduced to the spinal tissue in a range of reduction distance relative to the spinal tissue including engagement with the spinal tissue, partial or incomplete reduction and/or disposing the spinal rod at a selected dorsal height at any point along a length of a tether. In some embodiments, the present surgical system is employed for treating a large or hyperkyphosis or a spondylolisthesis reduction. In some embodiments, the present surgical system can be used for a translational correction technique. In some embodiments, the tether is used in a spondylolisthesis reduction to pull vertebrae towards the spinal rod.

In some embodiments, the present surgical system includes a pedicle screw, connectors, a tensioning device, and a spinal rod. In some embodiments, the pedicle screw includes a head having two loops for attachment of two tethers, such as, for example, 4 millimeter (mm) wide synthetic polyester fiber tape. In some embodiments, the pedicle screw includes a head having an anchor connected to the tether and being pivotable and/or rotatable in one or a plurality of axial directions relative to the pedicle screw. In some embodiments, the connector is engaged to the spinal rod and the tether to couple the spinal rod with the tether. In some embodiments, the connector locks the tape on the rod. In some embodiments, the connector locks the 4 mm tape to the spinal rod. In some embodiments, the tensioning device pulls the spinal rod along the tape towards the pedicle screw.

In some embodiments, the tensioning device includes a dispensing gun type configuration.

In some embodiments, the surgical system includes a tether and a connector configured to fix a posterior spinal rod to a spine by the tether such that the spinal rod is fixed in a flexible and/or dynamic configuration. In some embodiments, the tether and the connector are fixed with a spine at a top level of a spinal construct. In some embodiments, the spinal construct is fixed with a spine at one or a plurality of vertebral levels. In some embodiments, the tether and the connector are fixed to a spinal rod and maintains the tether in place after the tether is wrapped about vertebral tissue, such as, for example, a lamina. In some embodiments, the tether and the connector include one or a plurality of coupling members, such as, for example, set screws.

In some embodiments, the surgical system is used with surgical navigation, such as, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 2:
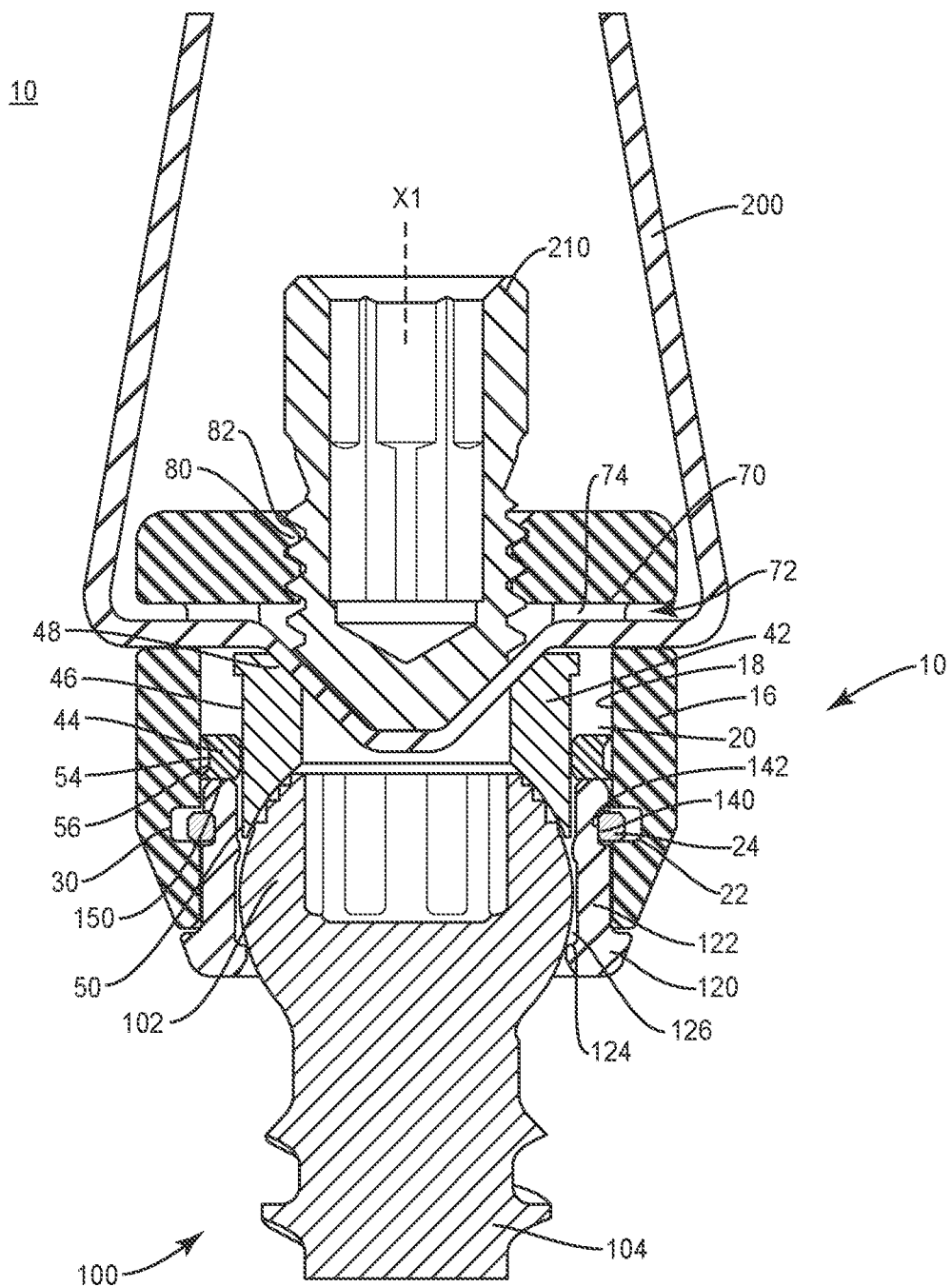
FIG. 2 is a cross section view of components of the system shown in FIG. 1.
Figure 3:
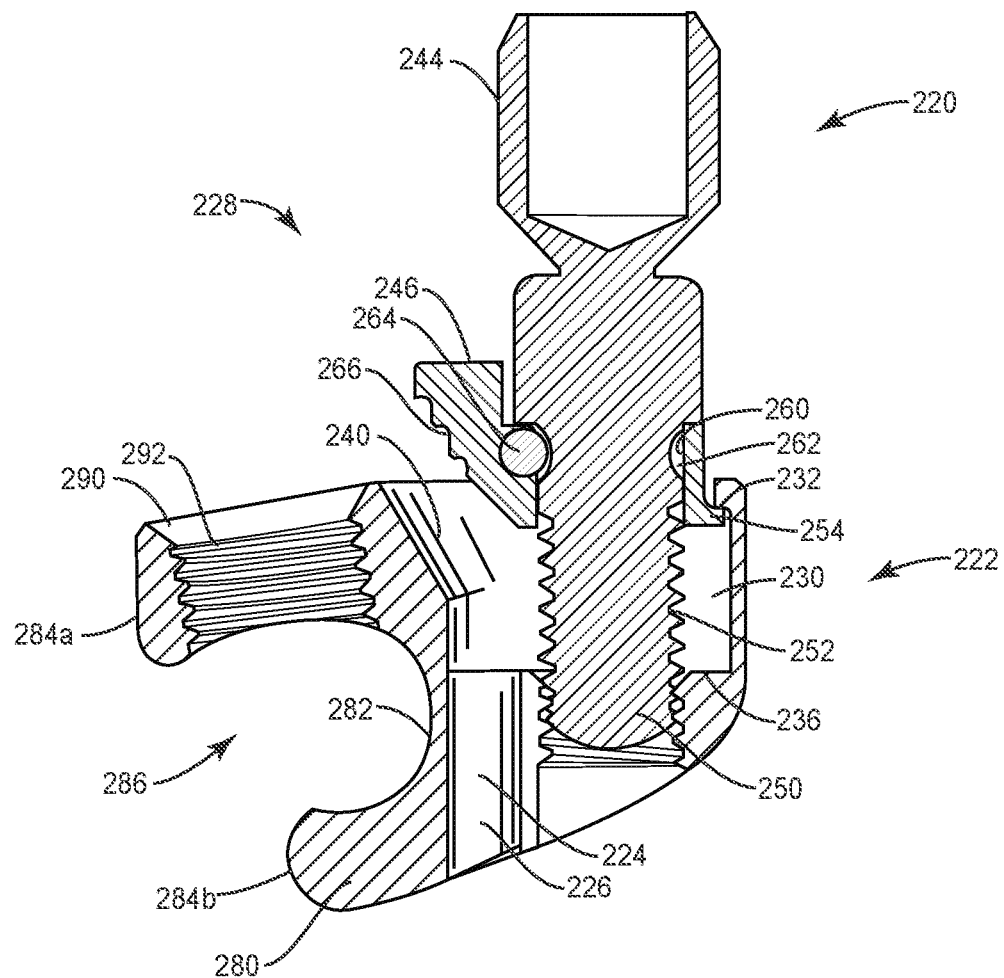
FIG. 3 is a cross section view of components of the system shown in FIG. 1.

The following discussion includes a description of a surgical system, which includes components and/or implants of a spinal construct, surgical instruments and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-3, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal construct 12. Spinal implant system 10 is employed, for example, with an open or mini-open, minimal access and/or minimally invasive including percutaneous surgical technique and includes one or more spinal constructs 12 for treatment at a surgical site within a body of a patient, for example, a section of a spine to treat various spine pathologies, such as those described herein. In some embodiments, the components of spinal implant system 10 are configured to deliver and introduce components of one or more spinal constructs 12 that include implants, such as, for example, one or more adaptors, receivers, spinal rods, bodies, sleeves, posts, connectors, plates and/or fasteners. Spinal construct 12 forms one or more components of a surgical treatment implanted with tissue for positioning and alignment to stabilize a treated section of vertebrae. In some embodiments, spinal construct 12 provides one or more selectively coupled components and/or implants to facilitate large dorsal reduction, as described herein. In some embodiments, spinal construct 12 includes a bone fastener configured for connection with a tether that allows a connector and/or a spinal rod connected therewith to be selectively reduced and/or disposed in a selected dorsal orientation relative to vertebral tissue.

Spinal construct 12 includes a fastener, such as, for example, a bone screw 100 connectable with a member, such as, for example, a receiver 14. Receiver 14 is configured for disposal of a tether 200, as described herein, and to provide a tether connection to bone screw 100. In some embodiments, receiver 14 employs tension and/or components to lock motion of bone screw 100 components and/or fixate position of tether 200 relative to bone screw 100, as described herein.

Receiver 14 includes a wall 16. Wall 16 includes an inner surface 18 that defines a cavity 20. Cavity 20 is configured for disposal of a head 102 of bone screw 100, as described herein. Wall 16 extends along an axis X1. In some embodiments, wall 16 may extend in alternate configurations relative to axis X1, such as, for example, arcuate, offset, staggered and/or angled portions. Cavity 20 is substantially circular. In some embodiments, all or only a portion of cavity 20 may have alternate cross section configurations, such as, for example, closed, V-shaped, W-shaped, oval, U-shaped, oblong, polygonal, irregular, uniform, non-uniform, offset, staggered, and/or tapered. In some embodiments, spinal construct 12 may include one or a plurality of receivers 14.

Surface 18 defines a groove 22 configured for disposal of a band, such as, for example, a circumferential ring 24. Ring 24 includes a circumference that extends between ends defining an opening, such as, for example, a gap (not shown), which facilitates expansion and contraction of ring 24. Groove 22 includes a portion, such as, for example, a circumferential channel 30. In some embodiments, bone screw 100 is manually engageable with receiver 14 and/or bone screw 100 is coupled with receiver 14 in a non-instrumented assembly such that ring 24 translates into channel 30, as described herein. Ring 24 is expandable and resilient between a contracted and/or capture orientation and an expanded orientation, as described herein. In some embodiments, ring 24 facilitates manual engagement of receiver 14 and bone screw 100 such that receiver 14 is attached with bone screw 100 in a non-instrumented assembly, as described herein.

Receiver 14 includes a part, such as, for example, a crown 42 and a sleeve 44 disposed with cavity 20. Crown 42 includes a wall 46 having an end surface 48 and an end surface 50. Surface 48 is configured for engagement with a longitudinal element, such as, for example, tether 200, as described herein. Surface 48 defines an engagement surface and/or a lock surface such that tether 200 is fixed with receiver 14 via compressive forces and/or friction forces applied by a coupling member, such as, for example, a set screw 210, as described herein. In some embodiments, the compressive forces applied by set screw 210 to tether 200, and/or to surface 48 may be directed in various orientations, such as, for example, perpendicular, transverse and/or at angular orientations, such as acute or obtuse.

Surface 50 defines a curved portion of crown 42 engageable with bone screw 100, as described herein. In some embodiments, all or only a portion of surface 50 may have alternate cross section configurations, such as, for example, oval, oblong, polygonal, irregular, uniform, non-uniform, offset, staggered, and/or tapered.

In some embodiments, spinal implant system 10 comprises a spinal implant kit, which includes alternate crowns, such as those described herein. In some embodiments, spinal implant system 10 comprises a spinal implant kit, which includes alternate receivers, screws and crowns. In some embodiments, receiver 14 is connected to a selected crown 42 to comprise a multi-axial receiver/bone screw component of spinal construct 12. In some embodiments, receiver 14 is connected to a selected crown 42 to comprise a uni-axial receiver/bone screw component of spinal construct 12. In some embodiments, receiver 14 is connected to a selected crown 42 to comprise a sagittally adjustable receiver/bone screw component of spinal construct 12. In some embodiments, receiver 14 is connected to a selected crown 42 to comprise a fixed axis receiver/bone screw component of spinal construct 12.

Sleeve 44 includes a surface 54 that defines a cavity, such as, for example, a groove 56. In some embodiments, groove 56 extends about all or a portion of surface 54. In some embodiments, groove 56 includes ramps selectively inclined to resist and/or prevent displacement of ring 24 from channel 30 to provisionally fix sleeve 44 with receiver 14. In some embodiments, the inclination of the ramps facilitate disengagement of ring 24 from groove 56 upon axial translation of sleeve 44, as described herein. In some embodiments, the ramps are oriented substantially perpendicular to axis X1. In some embodiments, groove 56 does not include inclined surfaces, as described above, and alternatively includes a protrusion or a lip configured to engage ring 24.

Sleeve 44 is configured for translation within cavity 20 along surface 18. Sleeve 44 translates relative to crown 42 and receiver 14 within cavity 20. Translation of sleeve 44 moves sleeve 44 between a configuration such that ring 24 is disposed within channel 30 and groove 56 to provisionally fix sleeve 44 relative to receiver 14 and a configuration, as shown in FIG. 2, such that ring 24 remains disposed within channel 30 and a base 120, attached with bone screw 100, to fix bone screw 100 with receiver 14, as described herein.

Figure 4:
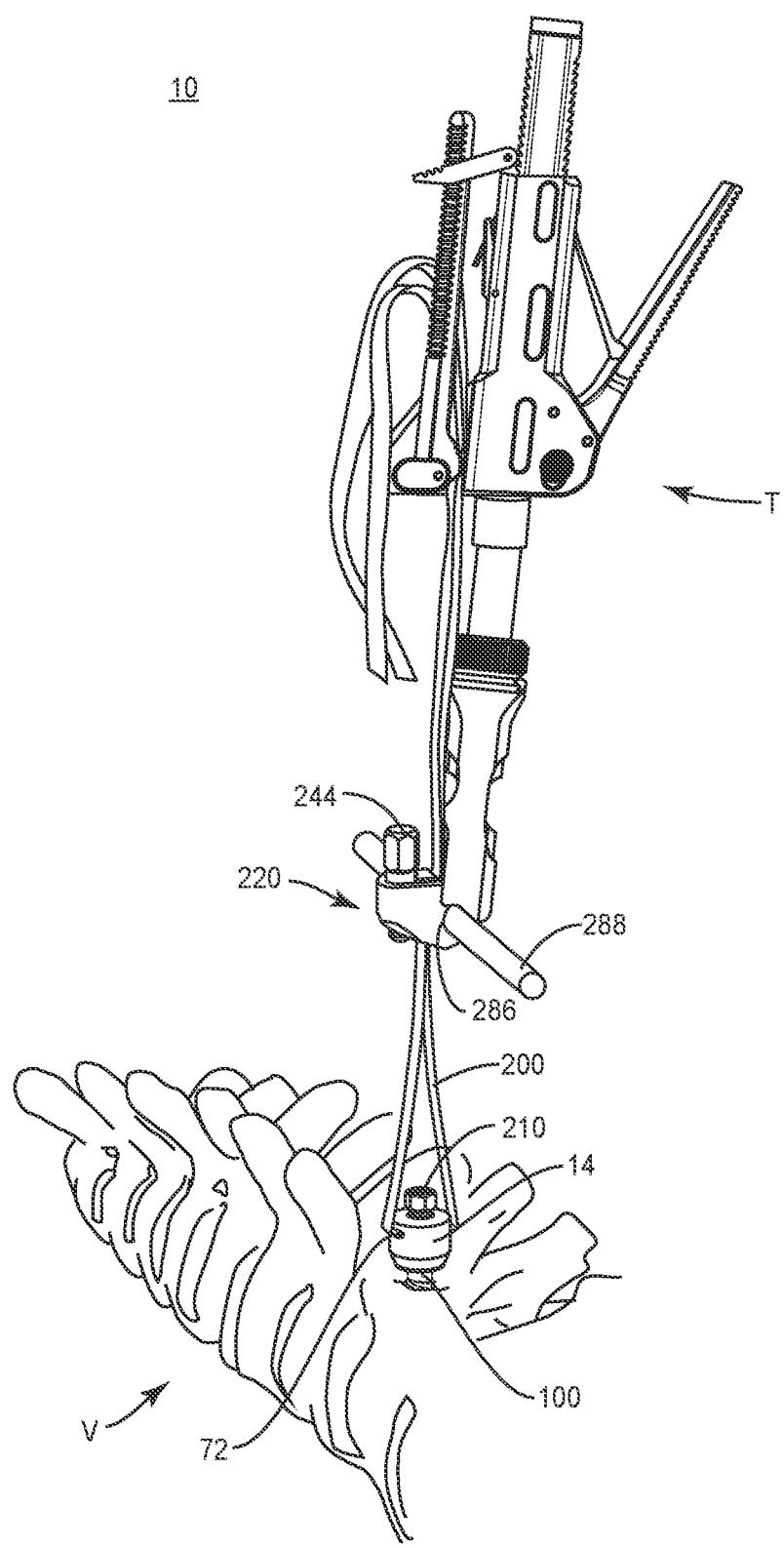
FIG. 4 is a perspective view of one embodiment of components of a surgical system in accordance with the principles of the present disclosure disposed with vertebrae.

Receiver 14 includes surface 70 that defines a passageway 72. Passageway 72 is configured for disposal of tether 200 such that tether 200 can be fixed or translate through passageway 72 and relative to receiver 14 and/or bone screw 100 for tensioning and/or adjustment. Passageway 72 includes a transverse slot 74 disposed in communication with surface 48. Tether 200 is configured for disposal with passageway 72 and surface 48 such that tether 200 captures a portion of receiver 14, as described herein. Disposal and/or fixation of tether 200 with passageway 72 positions a spinal implant, such as for example, spinal rod 288 and bone screw 100 in a selectively reduced orientation and/or disposes spinal rod 288 at a selected dorsal orientation and/or distance relative to vertebrae V (FIG. 4). The dorsal height between vertebral tissue and/or bone screw 100, and spinal rod 288 can be adjusted and/or selectively fixed along tether 200. In some embodiments, the selected fixation includes an incomplete or partial reduction of spinal rod 288 relative to vertebral tissue along tether 200.

Receiver 14 includes an inner surface 80. A portion of surface 80 includes a thread form 82. Thread form 82 is configured for engagement with set screw 210 such that set screw 210 is engaged with a surgical instrument to axially translate to engage tether 200 and/or crown 42 to selectively fix position and/or orientation of bone screw 100 relative to receiver 14, as described herein. In some embodiments, set screw 210 is configured to fix tether 200 relative to receiver 14 and/or bone screw 100. In some embodiments, surface 80 may be disposed with set screw 210 in alternate fixation configurations, such as, for example, friction fit, pressure fit, locking protrusion/recess, locking keyway and/or adhesive. In some embodiments, all or only a portion of surface 80 may have alternate surface configurations to enhance engagement with set screw 210, such as, for example, rough, arcuate, undulating, mesh, porous, semi-porous, dimpled and/or textured.

Bone screw 100 includes head 102 having a spherical configuration such that bone screw 100 is connected with receiver 14, for example, in a multi-axial configuration. Head 102 includes a surface 110 that defines a plurality of ridges to improve purchase of head 102 with crown 42. Head 102 includes a tool engaging portion configured to engage a surgical tool or instrument, as described herein. In some embodiments, the tool engaging portion includes a hexagonal cross-section to facilitate engagement with a surgical tool or instrument, as described herein. In some embodiments, the tool engaging portion may have alternative cross-sections, such as, for example, rectangular, polygonal, hexalobe, oval, or irregular.

Bone screw 100 includes base 120 configured for assembly with bone screw 100, as described herein. Base 120 includes a wall 122 having a surface 124. Surface 124 defines a cavity 126 configured for disposal of head 102. Surface 124 facilitates engagement of head 102 with base 120 via a pressure and/or force fit connection. In some embodiments, surface 124 includes mating elements, such as, for example, index elements (not shown). In some embodiments, the index elements include a protrusion (not shown) configured to limit rotation about a single axis disposed in a plane relative to receiver 14.

In some embodiments, base 120 may be disposed with head 102 in alternate fixation configurations, such as, for example, friction fit, pressure fit, locking protrusion/recess, locking keyway and/or adhesive. Base 120 is configured for rotation relative to head 102. In some embodiments, base 120 is configured for rotation in range of 360 degrees relative to head 102 to facilitate positioning of shaft 104 with tissue. In some embodiments, base 120 is configured for selective rotation in range of 360 degrees relative to and about head 102 such that shaft 104 is selectively aligned for rotation in a plane relative to receiver 14, and rotation in a second plane is resisted and/or prevented.

Wall 122 includes a surface 140. Surface 140 defines a groove 142. Groove 142 is configured for disposal of ring 24 to prevent displacement of ring 24 from channel 30 and to permanently fix receiver 14 with bone screw 100, as shown in FIG. 2. Base 120 is configured for axial translation relative to head 102, as described herein. For example, base 120 is assembled with head 102 and a surface 150 engages sleeve 44 to release sleeve 44 from ring 24. As base 120 engages sleeve 44 and translates, the ramp of groove 56 engages ring 24 and a surface of groove 56 slides over ring 24 to release sleeve 44 from ring 24. Ring 24 expands into channel 30. With ring 24 expanded into channel 30, base 120 and head 102 axially translate relative to receiver 14 within cavity 20 to align groove 142 with channel 30. Expansion of ring 24 facilitates axial translation of bone screw 100 into cavity 20. Alignment of groove 142 with channel 30 allows ring 24 to resiliently contract to the capture orientation for disposal of ring 24 within groove 142 and channel 30. Ring 24 is fixed within channel 30 and groove 142. The surfaces of groove 142 resist and/or prevent disengagement of ring 24 from channel 30 and groove 142 to permanently assemble bone screw 100 with receiver 14.

Shaft 104 is configured to penetrate tissue, such as, for example, bone. In some embodiments, shaft 104 includes an outer surface having an external thread form. In some embodiments, the external thread form may include a single thread turn or a plurality of discrete threads.

In some embodiments, receiver 14 is manually engageable with head 102 in a non-instrumented assembly, as described herein. In some embodiments, manual engagement and/or non-instrumented assembly of receiver 14 and head 102 includes coupling without use of separate and/or independent instrumentation engaged with the components to effect assembly. In some embodiments, manual engagement and/or non-instrumented assembly includes a practitioner, surgeon and/or medical staff grasping receiver 14 and bone screw 100 and forcibly assembling the components. In some embodiments, manual engagement and/or non-instrumented assembly includes a practitioner, surgeon and/or medical staff grasping receiver 14 and bone screw 100 and forcibly snap fitting the components together, as described herein. In some embodiments, manual engagement and/or non-instrumented assembly includes a practitioner, surgeon and/or medical staff grasping receiver 14 and bone screw 100 and forcibly pop fitting the components together and/or pop fitting receiver 14 onto bone screw 100, as described herein. In some embodiments, a force in a range of 2-50 N is required to manually engage receiver 14 and bone screw 100 and forcibly assemble the components. In some embodiments, a force in a range of 5-10 N is required to manually engage receiver 14 and bone screw 100 and forcibly assemble the components.

Spinal implant system 10 comprises a spinal implant, such as, for, example, a connector 220. Connector 220 includes a body 222 having a surface 224 that defines a cavity 226 configured for disposal of tether 200, as described herein. Cavity 226 is configured for movable disposal of a locking element 228 configured to fix tether 200 with body 222 between a non-locking orientation and a locked orientation, as described herein. In some embodiments, cavity 226 may have various cross section configurations, such as, for example, oval, oblong, triangular, rectangular, square, polygonal, irregular, uniform, non-uniform, variable and/or tapered. In some embodiments, surface 224 may include gripping elements or surfaces, such as, for example, rough, arcuate, undulating, mesh, porous, semi-porous, dimpled and/or textured to facilitate engagement with tether 200.

Surface 224 defines a slot 230 configured for engagement with a portion of a locking element 228, as described herein. Slot 230 includes a proximal end 232 and a distal end 236. Ends 232, 236 define a range of translation of locking element 228 as locking element 228 translates within cavity 226 between a non-locking orientation and a locked orientation.

Surface 224 defines a channel 240 in communication with cavity 226. Channel 240 is configured for disposal of tether 200. Tether 200 is configured for disposal with channel 240 between a movable configuration and a fixed configuration, as described herein. Tether 200 is fixed with surface 224 of channel 240 via compressive forces and/or friction force by locking element 228, as described herein. In some embodiments, the compressive forces applied by locking element 228, to tether 200, and/or to surface 224 may be directed in various orientations, such as, for example, perpendicular, transverse and/or at angular orientations, such as acute or obtuse.

Locking element 228 includes a screw 244 and a fixation element, such as, for example, a cleat 246. In some embodiments, screw 244 is fabricated from a fracturing and/or frangible material such that manipulation can fracture and separate a portion of screw 244 at a predetermined force and/or torque limit, as described herein. In some embodiments, as force and/or torque is applied to screw 244 and resistance increases, for example, due to fixation of screw 244 with cavity 226, as described herein, the predetermined torque and force limit is approached.

Screw 244 includes a shaft 250 having an outer surface 252. Surface 252 includes a thread form 254 configured for engagement with surface 224. In some embodiments, thread form 254 is continuous along surface 252. In some embodiments, thread form 254 may include a single thread turn or a plurality of discrete threads. In some embodiments, other penetrating elements may be located on shaft 250, such as, for example, a nail configuration, barbs, expanding elements, raised elements, ribs, and/or spikes to facilitate engagement of shaft 250.

Cleat 246 includes a surface 260 that defines a cavity 262. Cavity 262 is configured for disposal of screw 244. Screw 244 is connected with cleat 246 by retention pin 264. Retention pin 264 allows for rotation of screw 244 relative to cleat 246 to facilitate translation of cleat 246 into contact with tether 200 to engage and disengage cleat 246 with tether 200.

Cleat 246 includes a surface 266 oriented to engage tether 200 in a locked orientation, as described herein. In some embodiments, surface 266 may include penetrating members, such as, for example, a plurality of teeth. In some embodiments, the teeth may have various configurations, for example, round, oval, rectangular, polygonal, irregular, tapered, offset, staggered, uniform and non-uniform. Cleat 246 is engageable with screw 244 such that as screw 244 is actuated, cleat 246 includes a range of translation within cavity 226 and slot 230 to facilitate engagement and/or disengagement with tether 200 in a non-fixed and/or non-locking orientation with body 222 and a fixed and/or locked orientation with body 222. In the locked orientation, the teeth engage tether 200 to fix tether 200 with body 222. Surface 266 engages surface 224 to apply a compressive force and/or a friction force, as described herein, to fix tether 200 in a locked orientation.

Body 222 includes a wall 280 having a surface 282. Wall 280 includes extensions 284a, 284b. Extensions 284a, 284b define an opening, such as, for example, a bay 286 configured for disposal of spinal rod 288. In some embodiments, cavity 226 is disposed separate and apart from bay 286. In some embodiments, cavity 226 is disposed transverse to bay 286. In some embodiments, cavity 226 may be disposed in various orientations, such as, for example, perpendicular, transverse and/or at angular orientations, such as acute or obtuse relative to bay 286. In some embodiments, cavity 226 may be disposed offset or staggered from bay 286. In some embodiments, bay 286 may have various cross section configurations, such as, for example, oval, oblong, triangular, rectangular, square, polygonal, irregular, uniform, non-uniform, variable and/or tapered. In some embodiments, surface 282 may include gripping elements or surfaces, such as, for example, rough, arcuate, undulating, mesh, porous, semi-porous, dimpled and/or textured to facilitate engagement with spinal rod 288.

Body 222 includes a surface 290 that defines a cavity, such as, for example, an opening 292. Surface 290 is threaded and configured for disposal of a coupling member, such as, for example, a set screw 294. In some embodiments, set screw 294 includes an end having a hexagonal geometry configured for engagement with a similarly shaped surgical tool, such as, for example, a driver. In some embodiments, set screw 294 includes an end having a cruciform, phillips, square, hexalobe, polygonal or star cross sectional configuration for disposal of a correspondingly shaped portion of a driver. Set screw 294 is configured for engagement with spinal rod 288 to facilitate fixation and/or locking of spinal rod 288 with body 222.

Set screw 294 is disposable between a non-locking orientation, such that spinal rod 288 is translatable relative to body 222 and a locked orientation, such that set screw 294 fixes spinal rod 288 with body 222. In some embodiments, set screw 294 is fabricated from a fracturing and/or frangible material such that manipulation can fracture and separate a portion at a predetermined force and/or torque limit, as described herein.

In some embodiments, body 222 includes a mating surface 310 that defines cavities, such as, for example, mating capture elements 312 configured to mate with a surgical instrument to facilitate implant and manipulation of connector 220 and/or components of spinal implant system 10. In some embodiments, spinal implant system 10 may include one or a plurality of connectors 220 spaced apart and disposed along spinal rod 288, which may be relatively disposed in a side by side, irregular, uniform, non-uniform, offset and/or staggered orientation or arrangement, along one or a plurality of spinal rods 288. In some embodiments, spinal rod 288 extends along one or a plurality of vertebra, as described herein. In some embodiments, spinal implant system 10 may include one or a plurality of spinal rods 288, which may be relatively disposed in a side by side, irregular, uniform, non-uniform, offset and/or staggered orientation or arrangement.

Tether 200 extends between an end 316 and an end 318. Tether 200 is configured for engagement with the components of spinal construct 12, as described herein. End 316 and end 318 form a loop 320 configured for disposal with passageway 72 of receiver 14, as described herein. In some embodiments, tether 200 is configured to apply a tension to receiver 14 to fix receiver 14 relative to bone screw 100, such as, for example, to resist and/or prevent multi-axial movement of receiver 14 relative to bone screw 100. Tensioning of tether 200 is configured to position spinal rod 288 in a selectively reduced orientation and/or disposes spinal rod 288 at a selected dorsal orientation and/or distance relative to vertebrae V (FIG. 4), as described herein. In some embodiments, the dorsal height between bone screw 100 and spinal rod 288 is selectively fixed along tether 200. In some embodiments, the selected fixation includes an incomplete or partial reduction of spinal rod 288 relative to vertebral tissue along tether 200. In some embodiments, spinal implant system 10 may include one or a plurality of tethers 200, each tether 200 being configured for disposal about a single and separate vertebral level. In some embodiments, a single vertebral level may include one or a plurality of tethers 200.

Tether 200 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, the flexibility of tether 200 includes movement in a lateral or side to side direction and prevents expanding and/or extension in an axial direction upon tensioning and attachment with receiver 14. In some embodiments, all or only a portion of tether 200 may have a semi-rigid, rigid or elastic configuration, and/or have elastic properties, similar to the material examples described herein, such that tether 200 provides a selective amount of expansion and/or extension in an axial direction. In some embodiments, tether 200 may be compressible in an axial direction. Tether 200 can include a plurality of separately attachable or connectable portions or sections, such as bands or loops, or may be monolithically formed as a single continuous element.

Tether 200 can have a uniform thickness/diameter. In some embodiments, tether 200 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 200 may be uniformly increasing or decreasing, or have alternate diameter dimensions along its length. In some embodiments, tether 200 may have various cross section configurations, such as, for example, oval, oblong, triangular, rectangular, square, polygonal, irregular, uniform, non-uniform, variable and/or tapered. In some embodiments, the surface of tether 200 may include engaging structures, such as, for example, barbs, raised elements and/or spikes to facilitate engagement with tissue of the targeted anatomy.

In some embodiments, the surface of tether 200 may include a pliable lead. In some embodiments, tether 200 may include a pliable lead such that tether 200 can be passed and/or guided through components of spinal construct 12 and/or cavities of spinal tissue to resist and/or prevent non-desirable and/or harmful engagement with selected and/or sensitive anatomy of the spinal tissue. In some embodiments, the pliable lead is soft and flexible and configured to pass through a sub-laminar cavity of vertebrae without adhering to dura matter of a spinal cord and/or surfaces of a lamina of a vertebral level. In some embodiments, all or only a portion of the pliable lead is fabricated from a pliable, low-friction material, such as, for example, silicone, polyurethane, silicone-polyurethane copolymers, polymeric rubbers, polyolefin rubbers, elastomers, rubbers, thermoplastic elastomers, thermoset elastomers and elastomeric composites.

In some embodiments, tether 200 may have various lengths. In some embodiments, tether 200 may be braided, such as a rope, or include a plurality of elongated elements to provide a predetermined force resistance. In some embodiments, tether 200 may be made from autograft and/or allograft, and be configured for resorbable or degradable applications. In one embodiment, tether 200 is a cadaver tendon. In one embodiment, tether 200 is a tendon that may be harvested, for example, from a patient or donor. In some embodiments, a tendon harvested from a patient may be affixed in remote locations with the patient's body.

In assembly, operation and use, spinal implant system 10, similar to the systems and methods described herein, is employed with a surgical procedure, such as, for example, a correction treatment of an affected portion of a spine, for example, a correction treatment to treat adolescent idiopathic scoliosis and/or Scheuermann's kyphosis of a spine. In some embodiments, one or all of the components of spinal implant system 10 can be delivered or implanted as a pre-assembled device or can be assembled in situ. Spinal implant system 10 may be completely or partially revised, removed or replaced.

In use, to treat a selected section of vertebrae V, as shown in FIG. 4, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Pilot holes are made in vertebrae V in a selected orientation. Bone screws 100 are aligned with the pilot holes and fastened with the tissue of vertebrae V. Receiver 14 is pre-assembled with head 102 of bone screw 100 in a non-instrumented assembly on a back table of an operating room during a surgical procedure, as described herein. Assembly of receiver 14 with head 102 includes disposing crown 42 and sleeve 44 with slot 40, ring 24 with channel 30 and aligning head 102 and base 120 with receiver 14, as descried herein. Head 102 translates through and relative to ring 24 to move ring 24 into an expanded orientation, as described herein. Head 102 engages crown 42, sleeve 44 and ring 24 is resiliently biased to the capture orientation such that receiver 14 is attached with bone screw 100, as described herein. Disengagement of bone screw 100 from member 14 is resisted and/or prevented.

In some embodiments, receiver 14 can be assembled with bone screw 100 in-situ. For example, bone screw 100 is fastened with vertebrae V, as described herein, and receiver 14 is attached with head 102 in a non-instrumented assembly, as descried herein. Bone screw 100 including receiver 14 is aligned with a pilot hole and fastened with the tissue of vertebrae V.

Tether 200 is delivered along the surgical pathway to a surgical site adjacent receiver 14 and bone screw 100. Tether 200 is guided through passageway 72 for attachment with receiver 14 to capture receiver 14, as described herein. Tether 200 translates through passageway 72 for disposal with channel 240 and attachment with connector 220, as described herein. Screw 244 is rotated in a counter clockwise direction to dispose screw 244 in a non-locked orientation such that tether 200 is movable within channel 240.

Spinal rod 288 is disposed with bay 286. Set screw 294 is advanced into a non-locking orientation, as described herein. Spinal rod 288 is translatable relative to connector 220. The driver engages set screw 294 to fix spinal rod 288 with connector 220 for reduction of spinal rod 288 relative to bone screw 100 and vertebrae V via tether 200.

An actuator, such as, for example, a tensioner T is disposed adjacent connector 220. Tensioner T is aligned and engaged with mating capture elements 312 for releasable fixation and/or provisional fixation of tensioner T with connector 220. In some embodiments, tensioner T includes a ratchet mechanism to selectively tension tether 200. Tensioner T is actuated to tension tether 200. In some embodiments, the tension and/or tensile force applied to tether 200 and/or corrective forces applied to vertebrae V can be increased and/or decreased by tensioner T. Tensioning of tether 200 positions spinal rod 288 relative to bone screw 100 and/or vertebrae V in a selectively reduced orientation and/or disposes spinal rod 288 at a selected dorsal orientation and/or distance relative to vertebrae V. The dorsal height between bone screw 100 and/or vertebrae V, and spinal rod 288 is selectively fixed along tether 200 and/or can be adjusted with tensioner T to a selected distance or dorsal height relative to vertebrae V. In some embodiments, the selected fixation includes an incomplete or partial reduction of spinal rod 288 relative to tissue along tether 200.

Tether 200 is tensioned with tensioner T to selectively position spinal rod 288 relative to bone screw 100 and/or vertebrae V, as described herein. Set screw 210 is translated to engage tether 200 and crown 42 in a locking configuration to fix position of tether 200 relative to receiver 14 and/or bone screw 100, and orientation of receiver 14 relative to bone screw 100, corresponding to the selected position spinal rod 288 relative to bone screw 100 and/or vertebrae V. In some embodiments, tether 200 is tensioned with tensioner T to fix relative position of receiver 14 with bone screw 100 components and/or fixate position of tether 200 relative to receiver 14 and/or bone screw 100.

Screw 244 is engaged by a driver (not shown) for translation to actuate cleat 246. Cleat 246 is translated to engage tether 200. Surface 266 applies a compressive force and/or a friction force to fix tether 200 in a locked orientation with connector 220.

In some embodiments, spinal implant system 10 includes a second spinal rod 288 (not shown) delivered along the surgical pathway to the surgical site adjacent a contra-lateral side of vertebrae V. Second spinal rod 288 is connected with the contra-lateral side of vertebrae V via one or more tethers 200, similar to spinal rod 288 described herein. In some embodiments, spinal rod 288 and second spinal rod 288 are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters. Spinal implant system 10 may be completely or partially revised, removed or replaced.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal implant system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal implant system 10 may be used to prevent or minimize curve progression in individuals of various ages.

Figure 5:
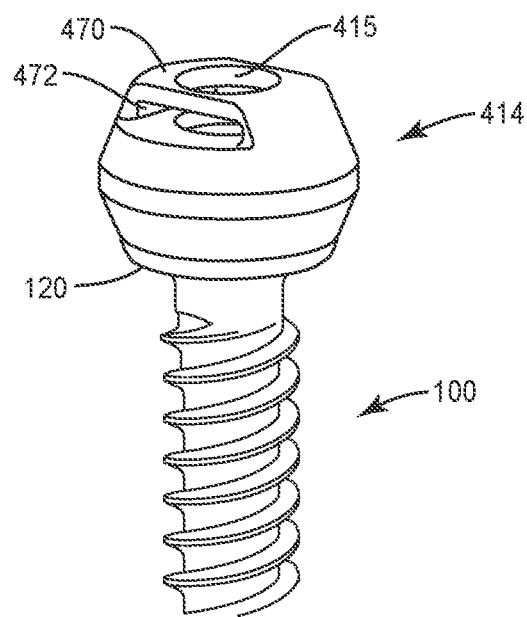
FIG. 5 is a perspective view of one embodiment of components of a surgical system in accordance with the principles of the present disclosure.
Figure 6:
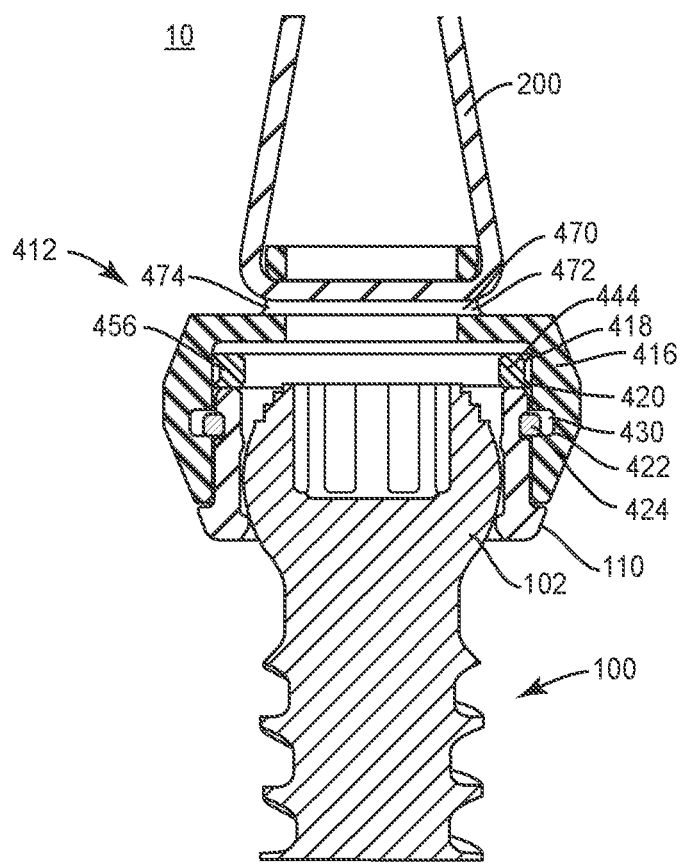
FIG. 6 is a cross section view of one embodiment of components of a surgical system in accordance with the principles of the present disclosure.
Figure 7:
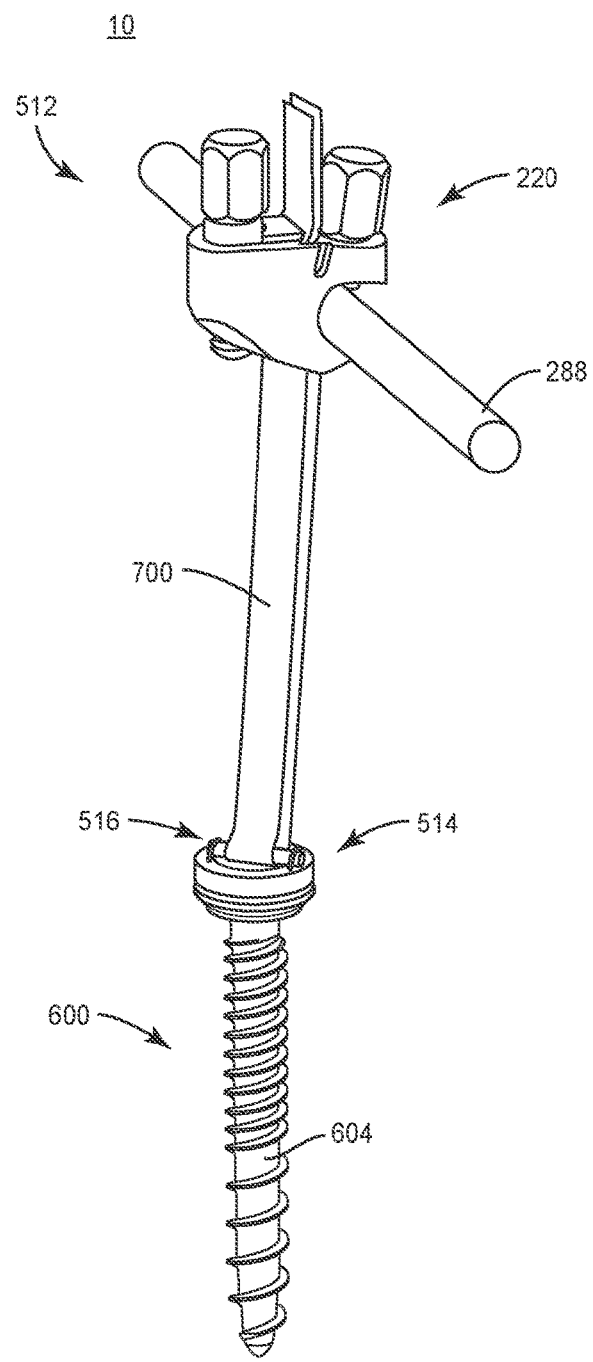
FIG. 7 is a perspective view of one embodiment of components of a surgical system in accordance with the principles of the present disclosure.
Figure 8:
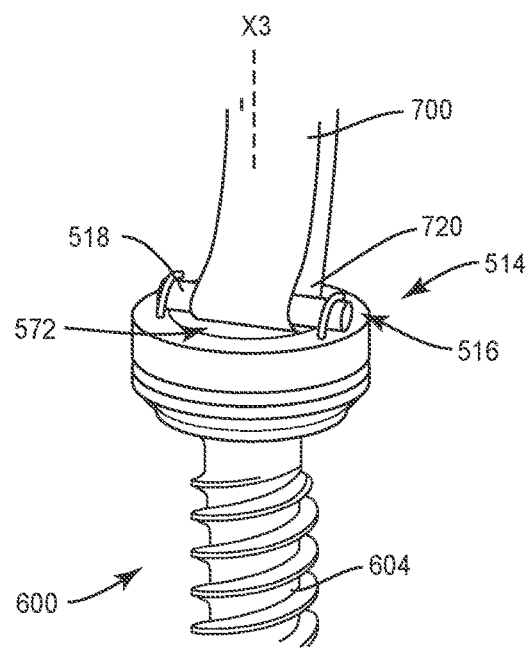
FIG. 8 is a break away view of components of the system shown in FIG. 7.
Figures 9, 10:
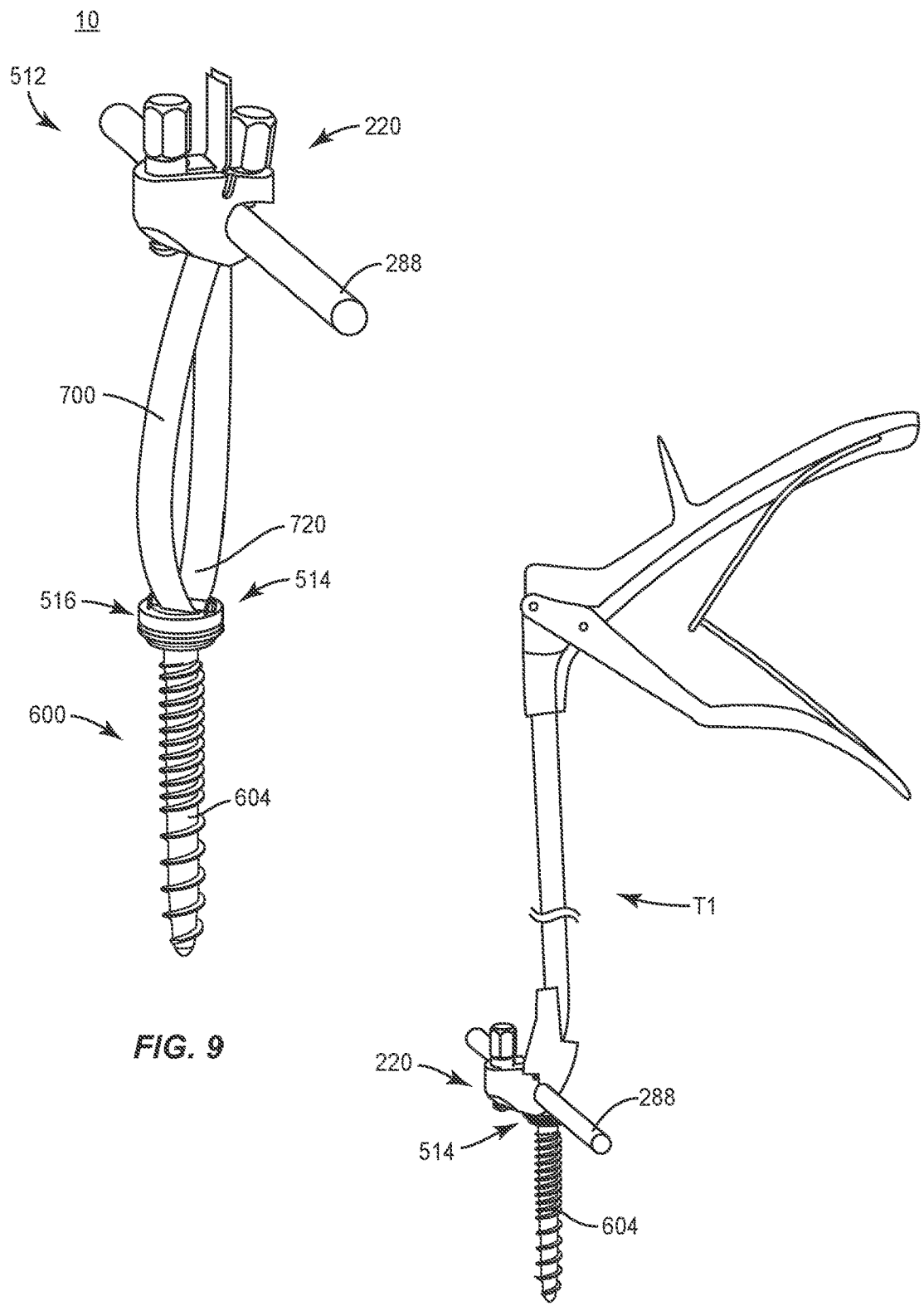
FIG. 9 is a perspective view of one embodiment of components of a surgical system in accordance with the principles of the present disclosure.
FIG. 10 is a perspective view of one embodiment of components of a surgical system in accordance with the principles of the present disclosure.

In one embodiment, as shown in FIGS. 5 and 6, spinal implant system 10, similar to the systems and methods described herein, includes a spinal construct 412, similar to spinal construct 12 described herein. Spinal construct 412 includes a receiver 414, similar to receiver 14 described herein. Receiver 414 is configured for connection and disposal of bone screw 100 and tether 200, as described herein. Receiver 414 includes an opening 415 that provides access to bone screw 100.

Receiver 414 includes a wall 416. Wall 416 includes an inner surface 418 that defines a cavity 420. Cavity 420 is configured for disposal of base 120 and head 102 of bone screw 100, similar to that described herein. Surface 418 defines a groove 422 configured for disposal of a ring 424, similar to ring 24 described herein. Groove 422 includes a channel 430, similar to channel 30 described herein. Ring 424 is expandable and resilient between a contracted and/or capture orientation and an expanded orientation, as described herein. Receiver 414 includes a sleeve 444, similar to sleeve 44 described herein, disposed with cavity 420.

Receiver 414 includes a bracket 470 that defines a passageway 472, similar to passageway 72 described herein. Passageway 472 is configured for disposal of tether 200 such that tether 200 can be fixed or translated through passageway 472 and relative to receiver 414 and/or bone screw 100 for tensioning and/or adjustment. Passageway 472 includes a transverse slot 474. Tether 200 is configured for disposal with passageway 472 such that tether 200 captures a portion of receiver 414, as described herein. Disposal and/or fixation of tether 200 with passageway 472 positions spinal rod 288 and bone screw 100 in a selectively reduced orientation and/or disposes spinal rod 288 at a selected dorsal orientation and/or distance relative to vertebral tissue and/or bone screw 100, similar to that described herein.

Tether 200 is tensioned with an actuator, similar to those described herein, such that tether 200 is drawn in tension with receiver 414. Tension forces and/or friction forces applied to tether 200 are transmitted to bracket 470 to fix relative position of receiver 414 with bone screw 100 components and to fix position of tether 200 relative to receiver 14 and/or bone screw 100. Tether 200 can be tensioned in a locking configuration to fix position of tether 200 relative to receiver 414 and/or bone screw 100, and orientation of receiver 414 relative to bone screw 100, corresponding to a selected position of spinal rod 288 relative to bone screw 100 and/or vertebral tissue, similar to that described herein.

In one embodiment, as shown in FIGS. 7-10, spinal implant system 10, similar to the systems and methods described herein, includes a spinal construct 512, similar to spinal construct 12 described herein. Spinal construct 512 includes a receiver 514, similar to receiver 14 described herein. Receiver 514 is engageable with a bone screw 600, similar to bone screw 100 described herein, and a tether 700, similar to tether 200 described herein.

Receiver 514 includes a swivel 516 that rotates about an axis X3 of bone screw 600 such that receiver 514 is rotatable relative to a shaft 604 in one or a plurality of axial directions. Swivel 516 has a disc-shaped configuration. Swivel 516 includes an anchor 518 connected with loop 720 of tether 700, as described herein, such that receiver 514 rotates tether 700 in one or a plurality of axial orientations. Anchor 518 includes a passageway 572, similar to passageway 72 described herein, configured for disposal of tether 700. Tether 700 includes 4 mm wide synthetic polyester fiber tape.

Tether 700 is configured for disposal with passageway 572 such that tether 700 captures a portion of receiver 514, similar to that described herein. Disposal and/or fixation of tether 700 with passageway 572 positions spinal rod 288 and bone screw 600 in a selectively reduced orientation and/or disposes spinal rod 288 at a selected dorsal orientation and/or distance relative to vertebral tissue and/or bone screw 600, similar to that described herein.

An actuator, such as, for example, a tensioner T1, similar to tensioner T described herein, is configured for disposal and engagement with tether 700 for tensioning tether 700 and connecting and/or reducing the components of spinal construct 512 with vertebral tissue and/or bone screw 600. Tensioner T1 includes a ratchet mechanism (not shown), for example, a gear or angled teeth and a pawl that allow motion in one direction and prevent motion in an opposing direction, which is engageable with tether 700. Tether 700 is tensioned with the ratchet mechanism of tensioner T1 such that tether 700 is drawn in tension with receiver 514. Tension forces and/or friction forces applied to tether 700 are transmitted to anchor 518 to fix relative position of receiver 514 with bone screw 600 components and to fix position of tether 700 relative to receiver 514 and/or bone screw 600. Tether 700 can be tensioned in a locking configuration to fix position of tether 700 relative to receiver 514 and/or bone screw 600, and orientation of receiver 514 relative to bone screw 600, corresponding to a selected position of spinal rod 288 relative to bone screw 600 and/or vertebral tissue, similar to that described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a fastener including a head and defining a longitudinal axis;
    a band;
    a member configured for disposal of the head and defining a cavity and an inner groove configured for disposal of the band, the member being moveable relative to the longitudinal axis, the member defining a passageway configured for disposal of a tether;
    a sleeve disposed in the cavity and defining a first outer groove; and
    a base disposed in the cavity and defining a second outer groove,
    wherein the sleeve is configured to translate axially between a first configuration in which the band is disposed in the inner groove and the first outer groove to provisionally fix the sleeve relative to the member and a second configuration in which the band is disposed in the inner groove and the second outer groove to fix the fastener with the member.

2. A spinal implant as recited in claim 1, wherein:
    the member comprises a proximal surface defining a circular opening that is coaxial with the cavity; and
    the spinal implant further comprises a coupling member disposable in the circular opening to selectively fix orientation of the fastener relative to the member.

3. A spinal implant as recited in claim 2, wherein the coupling member is engageable with the tether to fix position of the tether relative to the member and the head.

4. A spinal implant as recited in claim 2, further comprising a crown disposable between the coupling member and the head such that the coupling member engages the crown to selectively fix orientation of the fastener relative to the member, an inner surface of the sleeve directly engaging an outer surface of the crown when the sleeve is in the second configuration.

5. A spinal implant as recited in claim 1, wherein the tether is tensioned to fix orientation of the fastener relative to the member.

6. A spinal implant as recited in claim 1, wherein the passageway includes only one transverse slot, the transverse slot extending in a single plane through opposite sides of the member.

7. A spinal implant as recited in claim 1, wherein the member is engageable with the head in a snap-fit assembly.

8. A spinal implant as recited in claim 1, wherein the base directly engages the sleeve and translates axially with the sleeve as the sleeve moves from the first configuration to the second configuration.

9. A spinal implant as recited in claim 1, wherein the fastener includes a shaft for penetrating tissue and the head is rotatable relative to the shaft.

10. A spinal implant as recited in claim 1, wherein the member comprises a proximal surface defining a threaded circular opening that is coaxial with the cavity, the threaded circular opening being configured for disposal and engagement with a set screw, the sleeve being positioned between an uppermost surface of the base and the proximal surface.

11. A spinal implant as recited in claim 1, wherein the tether comprises tape.

12. A spinal implant system comprising:
    a connector defining a cavity and a bay, the cavity having a locking element movably disposed therein, the locking element comprising a screw and a cleat, the screw comprising an outer thread form configured for engagement with an inner thread form of the connector, the cleat comprising an aperture, the screw extending through the aperture;
    a tether configured for disposal within the cavity, the screw being connected with the cleat by a retention pin to allow the screw to rotate relative to the cleat to facilitate rotation of the cleat into contact with the tether to engage and disengage the cleat with the tether;
    a spinal rod configured for disposal within the bay;
    a fastener including a head and defining a longitudinal axis; and
    a member configured for disposal of the head and defining an inner groove configured for disposal of a band that is engageable with the head to connect the fastener and the member, the member being moveable relative to the longitudinal axis, the member defining a passageway configured for disposal of the tether.

13. A spinal implant system as recited in claim 12, further comprising an actuator connected with the connector and being engageable with the tether to incrementally tension the tether.

14. A spinal implant system as recited in claim 13, wherein the actuator includes a ratchet engageable with the tether.

15. A spinal implant system as recited in claim 12, wherein the member is disposable a selected dorsal height relative to the spinal rod along the tether, the selected dorsal height being adjustable.

16. A spinal implant system as recited in claim 12, further comprising a coupling member disposable with the member and the head to selectively fix orientation of the fastener relative to the member.

17. A spinal implant system as recited in claim 16, wherein the coupling member is engageable with the tether to fix position of the tether relative to the member and the head.

18. A spinal implant system as recited in claim 12, wherein the tether is tensioned to fix orientation of the fastener relative to the member.

19. A spinal implant system comprising:
    a connector defining a cavity and a bay, the cavity having a locking element movably disposed therein, the locking element comprising a screw and a cleat, the screw comprising an outer thread form configured for engagement with an inner thread form of the connector, the cleat comprising an aperture, the screw extending through the aperture;

a tether configured for disposal within the cavity, the screw being connected with the cleat by a retention pin to allow the screw to rotate relative to the cleat to facilitate rotation of the cleat into contact with the tether to engage and disengage the cleat with the tether;

a spinal rod configured for disposal within the bay;

a fastener including a head and defining a longitudinal axis;

a member configured for disposal of the head and defining an inner groove configured for disposal of a band that is engageable with the head to connect the fastener and the member, the member being moveable relative to the longitudinal axis, the member defining a passageway configured for disposal of the tether; and a tensioner connected with the connector and including a ratchet engageable with the tether to adjust tension of the tether.

20. A spinal implant system as recited in claim 19, wherein the member is disposable a selected dorsal height relative to the spinal rod along the tether, the selected dorsal height being adjustable.

* * * * *

UNITED STATES PATENT AND TRADEMARK OFFICE
CERTIFICATE OF CORRECTION

PATENT NO. : 10,292,737 B2
APPLICATION NO. : 15/616397
DATED : May 21, 2019
INVENTOR(S) : Rice et al.

Page 1 of 1

It is certified that error appears in the above-identified patent and that said Letters Patent is hereby corrected as shown below:

In the Claims

In Column 18, Line 46, in Claim 15, delete "disposable a selected" and insert -- disposable at a selected --, therefor.

In Column 19, Line 19, in Claim 20, delete "disposable a selected" and insert -- disposable at a selected --, therefor.

Signed and Sealed this
Seventeenth Day of September, 2019

Andrei Iancu
*Director of the United States Patent and Trademark Office*